United States Patent [19]

Toohey

[11] Patent Number: 4,751,285

[45] Date of Patent: Jun. 14, 1988

[54] DERIVATIVE OF COBALAMIN CONTAINING PERSULFIDE SULFUR AND GLUTATHIONE

[76] Inventor: John I. Toohey, R.R. 1, Elgin, Ontario, Canada, K0G 1E0

[21] Appl. No.: 917,351

[22] Filed: Oct. 9, 1986

[51] Int. Cl.$^4$ .............................................. C07K 5/08
[52] U.S. Cl. .................................................... 530/331
[58] Field of Search ........................................ 530/331

[56] References Cited

PUBLICATIONS

Chem. Abstr., vol. 83, No. 74525k, 1975 (Harada et al., Abstract of Vitamins 49, pp. 207–210, 1975).
Chem. Abstr., vol. 83, No. 74439k, 1975 (Harada et al., Abstract of Vitamins 49, pp. 201–206, 1975).

*Primary Examiner*—John Kight
*Assistant Examiner*—Christina Chan

[57] ABSTRACT

The combination of a cobamide compound, sulfide ion, and glutathione under appropriate conditions leads to the formation of a complex of the three reagents in which sulfur is present as stable persulfide.

1 Claim, No Drawings

DERIVATIVE OF COBALAMIN CONTAINING PERSULFIDE SULFUR AND GLUTATHIONE

BACKGROUND OF THE INVENTION

1. Field of the Invention

The invention is in the field of Vitamin $B_{12}$ derivatives. The unique properties of the cobamide molecule ("cobamide" used in the generic sense) and glutathione (GSH) are utilized to serve as a means of stabilizing and transporting persulfide sulfur (R-S-$\underline{S}^{-1}$).

2. Description of the Prior Art

Persulfide sulfur has recently been recognized has a regulator of cellular proliferation (1). Since low-molecular-weight persulfides are very unstable at pH near 7, the useful application of persulfides has previously required the use of systems which continuously generate persulfide sulfur in situ (1). Because of the complexity of these systems, it is desirable to replace them with a stable source of preformed persulfide sulfur.

The reaction of the sulfide, or hydrosulfide, ion with the cobalt atom of cobamide compounds has been reported (2-4). However, the Co-S bond is unstable and the compounds decompose rapidly in the presence of air to give the aquocobamide and colloidal sulfur. Sulfhydryl compounds (R-SH) also react in a similar manner to give somewhat more stable purple-colored derivatives (2,5). In the presence of air, these purple derivatives oxidize readily to regenerate the aquocobamide and the oxidized product R-S-S-R. The simultaneous addition of sulfide ion and GSH to a cobamide compound has not been previously reported and the unique stable product is novel.

It should be noted that Kaczka et al. reported a product from the reaction of $H_2S$ with cyanocobalamin which, on exposure to air, reverted to a red compound with the properties of aquocobalamin (4). They stated that the red compound was found to contain sulfur by elemental analysis but that the sulfur was not detectable as sulfide, sulfite, or sulfate. This work is not reproducible and it is now clear that their red product was, in fact, aquocobalamin contaminated with super-fine colloidal sulfur which was not removed by filtration and which precipitated during crystallization of the cobalamin.

DESCRIPTION OF THE INVENTION

When aquocobalamin, hydrosulfide ion, and GSH are combined in that order at pH near 7, an orange-brown product is formed (Table). The initial color change on adding HS$^-$ to the cobamide is to purple but this very rapidly turns to brown. The cobamide product can be freed of excess HS$^-$ and GSH by passage through a column of the anion exchange resin, AG-3 in the chloride form. Analysis of the product in a diffusion assay in which labile sulfur is released by excess cysteine and measured by diffusion into a color reagent (7) shows that the product contains labile sulfur.

TABLE

Reaction of Aquocobalamin (OHB$_{12}$), Na$_2$S, and GSH at pH 7

| Conditions | Color of mixture before GSH | Color of mixture after GSH | Color of mixture after AG-3 | Labile S in product |
|---|---|---|---|---|
| complete system | brown | red-brown | orange-brown | + |
| OHB$_{12}$ omitted | no color | — | — | — |
| Na$_2$S omitted | red | purple | purple → red | — |
| GSH omitted | brown | — | red | — |
| OHB$_{12}$ replaced by aquocobinamide | brown | red-brown | orange-brown | + |
| OHB$_{12}$ replaced by CN, CH$_3$, or coenzyme B$_{12}$ | red | red | red | — |
| GSH replaced by G—S—S—G | brown | red-brown | orange-brown | + |
| GSH replaced by cysteine | brown | red-brown | orange | — |
| Na$_2$S replaced by Na$_2$S$_2$, Na$_2$S$_2$O$_3$, or elemental S | | red-brown | orange-brown | + |

If any of the three reactants is omitted, the product does not contain labile sulfur. The aquocobalamin can be replaced with aquocobinamide (Factor B) but not by cyano or methyl cobalamin or by coenzyme $B_{12}$. Na$_2$S can be replaced by polysulfide, thiosulfate, or elemental sulfur. The exact nature of the sulfur reactant is not known but in the complicated redox equilibrium of the reaction mixture, where all three reactants as well as atmospheric oxygen undergo facile oxidation-reduction reactions, the reactive sulfur species is apparently generated from any of the named sources. Similarly, in systems containing the reduced species of sulfur (HS$^-$ or HSS$^-$), oxidized glutathione can be used in place of the reduced form. GSH cannot be replaced by other sulfhydryl compounds such as cysteine, cysteamine, or mercaptoethanol.

The following is a description of the preparation of the stable complex from aquocobinamide (Factor B). Aquocobinamide (prepared from cyanocobalamin or hydroxycobalamin by hydrolysis in 12N HCl at 65° for 5 minutes), 100 mg dissolved in 10 ml of water, is mixed with an aqeous solution containing 0.5 mmol of Na.polysulfide (prepared by dissolving elemental sulfur in aqueous Na$_2$S at a molar ratio of 1:1). The pH of the mixture is adjusted to 7 with HCl and buffered at that value with 0.01M Na.phosphate. A solution containing 0.5 mmol of GSH at pH 6.8 is added. The mixture is allowed to stand in the dark for 3 hours. It is then passed through a 10 c.c. column of anion exchange resin, Biorad AG-3 chloride form, to remove excess sulfides and GSH. The pH of the passthrough is adjusted to 7 and acetone is added slowly until the acetone:water ratio is 10:1. The mixture is allowed to stand for several hours while crystallization occurs. The crystals are washed twice with acetone and dried.

The product has the following properties. Aqueous solutions are orange-brown in color; the absorption spectrum shows a broad maximum at 330 nm with other peaks at 235 and 425 nm and shoulders at 490 and and 630 nm. This spectrum is very much different from spectra of all known classes of B$_{12}$ compounds. The compound is positively charged and is retained by cation exchange resins. It contains cobinamide, glutathione, and labile sulfur in a ratio of 1:1:1. The GSH is readily measured by the ninhydrin method; it is firmly bound in the complex since it is not removed by anion exchange resins. The labile sulfur is measured by the diffusion assay (as described above) or by cyanolysis. In the latter assay, addition of $CN^-$ ion causes the formation of dicyanocobinamide which is removed on a cation exchange resin. When the passthrough is mixed with $Fe(NO_3)_3$ reagent, it gives a red color characteristic of $SCN^-$ formed from persulfide in the presence of $CN^-$. The compound supports in vitro proliferation of persulfide-dependent L1210 cells (1).

References cited

1. Toohey, J. I., Biochem. Cell. Biol. in press Aug. issue (1986).
2. Adler, N., Medwick, T., Poznanski, T. J., J. Am. Chem. Soc., 88, 5018 (1966).
3. Dolphin, D. H., Johnson, A. W., Chem. Soc. Proc., 311 (1963).
4. Kaczka, E. A., Wolf, D., Kuehl, F. A., Folkers, K., J. Am. Chem. Soc., 73, 3569 (1951).
5. Dubnoff, J. W., Biochem. Biophys. Res. Commun., 16, 484 (1964).
6. Rao, G. S., Gorin, G., J. Org. Chem., 24, 749 (1959).
7. Toohey, J. I., Arch. Biochem. Biophys., 223, 533 (1983).

What is claimed is:

1. A stable sulfide-containing derivative of cobalamin prepared by combining aquocobalamin or aquocobinamide in water with a 5-fold molar ratio of sulfur in the form of sulfide ion, polysulfide ion, thiosulfate, or elemental sulfur and a 5-fold molar ratio of glutathione at pH 7, removing the excess sulfur and glutathione reactants with anion exchange resin, and precipitating the product by addition of acetone.

* * * * *